(12) United States Patent
Ohashi et al.

(10) Patent No.: US 11,828,889 B2
(45) Date of Patent: Nov. 28, 2023

(54) SCINTILLATOR UNIT AND RADIATION DETECTOR

(71) Applicant: CANON KABUSHIKI KAISHA, Tokyo (JP)

(72) Inventors: Yoshihiro Ohashi, Tokyo (JP); Satoshi Yamabi, Kanagawa (JP); Yoshinori Kotani, Kanagawa (JP); Nobuhiro Yasui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 8 days.

(21) Appl. No.: 17/585,390

(22) Filed: Jan. 26, 2022

(65) Prior Publication Data

US 2022/0146694 A1    May 12, 2022

Related U.S. Application Data

(63) Continuation of application No. PCT/JP2020/029187, filed on Jul. 30, 2020.

(30) Foreign Application Priority Data

Jul. 31, 2019  (JP) .................................. 2019-141821

(51) Int. Cl.
*G01T 1/20* (2006.01)

(52) U.S. Cl.
CPC .......... *G01T 1/2006* (2013.01); *G01T 1/2002* (2013.01)

(58) Field of Classification Search
CPC ... G01T 1/2006; G01T 1/2002; G01T 1/2012; G01T 1/202; A61B 6/00; A61B 6/40; G21K 4/00
See application file for complete search history.

(56) References Cited

U.S. PATENT DOCUMENTS

| 4,311,907 A | * | 1/1982 | Takami | ................. | G01T 1/2002 |
| | | | | | 250/487.1 |
| 2004/0179029 A1 | | 9/2004 | Ogawa et al. | | |
| 2007/0051896 A1 | * | 3/2007 | Okada | ................... | G01T 1/2018 |
| | | | | | 250/370.11 |
| 2013/0284933 A1 | * | 10/2013 | Nakatsugawa | ......... | G01T 1/202 |
| | | | | | 250/361 R |
| 2019/0004186 A1 | * | 1/2019 | Kotake | ................. | G01T 1/2002 |

FOREIGN PATENT DOCUMENTS

| JP | H11202053 A | 7/1999 |
| JP | 2001-516888 A1 | 10/2001 |
| JP | 2009222578 A | 10/2009 |
| JP | 2014032029 A | 2/2014 |
| JP | 2014077735 A | 5/2014 |
| JP | 6101443 B2 * | 3/2017 |
| WO | 2008/149659 A1 | 12/2008 |
| WO | 2017047411 A1 | 3/2017 |
| WO | 2016167334 A1 | 2/2018 |

* cited by examiner

*Primary Examiner* — Kiho Kim
(74) *Attorney, Agent, or Firm* — Canon U.S.A., Inc., IP Division (57) ABSTRACT

A scintillator unit with less light leakage from a scintillator to an adhesive layer and a radiation detector that can improve sensitivity to radiation and the resolution of an image to be formed. Specifically disclosed is a scintillator unit including an adhesive layer between a scintillator and a supporting member and a low-refractive-index layer with a lower refractive index than the adhesive layer between the scintillator and the adhesive layer.

16 Claims, 5 Drawing Sheets

SCINTILLATOR UNIT AND RADIATION DETECTOR

CROSS-REFERENCE TO RELATED APPLICATIONS

This application is a Continuation of International Patent Application No. PCT/JP2020/029187, filed Jul. 30, 2020, which claims the benefit of Japanese Patent Application No. 2019-141821, filed Jul. 31, 2019, both of which are hereby incorporated by reference herein in their entirety.

TECHNICAL FIELD

The present disclosure relates to a scintillator unit and a radiation detector.

BACKGROUND ART

A radiation detector is used to photograph an object by radiation in medical settings and the like and is composed mainly of a scintillator, which generates light by radiation (for example, X-rays), and a detecting unit including two-dimensionally arranged light-receiving devices. When the object is irradiated with X-rays, X-rays passing through the object generate light from the scintillator, and the detecting unit detects the light and forms a two-dimensional image of the transmitted X-rays.

A columnar crystal group containing a plurality of columnar crystals is used as a scintillator to efficiently transmit light generated by the scintillator to a light-receiving device and to improve the sensitivity of the radiation detector to radiation. A space containing air is formed between the columnar crystals in the columnar crystal group. When alkali halide crystals, such as cesium iodide (CsI), are used as columnar crystals, light entering a space containing air with a low refractive index from the columnar crystals with a high refractive index does not pass through but is reflected at the interface between the columnar crystals and the space. Thus, even if light generated from the scintillator is emitted in any direction, a physical phenomenon "total reflection" caused by a refractive index difference between two media is utilized to guide light generated in the columnar crystals to the detecting unit.

Furthermore, to guide most of light generated from the scintillator to the detecting unit, a reflective layer may be provided via an adhesive layer on a surface of the scintillator opposite the detecting unit. For example, Patent Literature 1 describes a flat-panel detector (FPD) including an air layer, a dielectric multilayer reflective film, an adhesive layer, a phosphor layer, and a photodetector in this order in the incident direction of radiation.

The present inventors have studied the FPD described in Patent Literature 1 using a columnar crystal group containing CsI (refractive index=1.74) as the phosphor layer and a layer containing an acrylic resin (refractive index=1.45) as the adhesive layer. As a result, it was found that light generated from columnar crystals contained in the phosphor layer is difficult to reflect at the interface between the phosphor layer and the adjacent adhesive layer and leaks into the adhesive layer.

It was also found that light incident on the adhesive layer attenuates in the adhesive layer, thus leaving room for further improvement in sensitivity to radiation.

It was also found that light generated from a columnar crystal contained in the phosphor layer propagates and diffuses in the adhesive layer and then enters another columnar crystal, thus leaving room for further improvement in the sharpness (resolution) of an image to be formed.

CITATION LIST

Patent Literature

PTL 1: International Publication No. WO 2016/167334

SUMMARY OF INVENTION

Accordingly, it is an aspect of the present disclosure to provide a scintillator unit with less light leakage from a scintillator into an adhesive layer. It is another aspect of the present disclosure to provide a radiation detector in which the scintillator unit can be used to improve sensitivity to radiation and the resolution of an image to be formed.

The present disclosure relates to a scintillator unit including an adhesive layer between a scintillator and a supporting member, wherein a low-refractive-index layer with a lower refractive index than the adhesive layer is located between the scintillator and the adhesive layer.

The present disclosure also relates to a radiation detector including: a scintillator unit including an adhesive layer between a scintillator and a supporting member; and a detecting unit for detecting light generated from the scintillator, wherein the scintillator unit includes a low-refractive-index layer with a lower refractive index than the adhesive layer between the scintillator and the adhesive layer, and the detecting unit faces the low-refractive-index layer via the scintillator.

Further features of the present disclosure will become apparent from the following description of exemplary embodiments with reference to the attached drawings.

DESCRIPTION OF EMBODIMENTS

A scintillator unit according to the present disclosure includes an adhesive layer between a scintillator and a supporting member. A scintillator unit according to the present disclosure further includes a low-refractive-index layer with a lower refractive index than the adhesive layer between the scintillator and the adhesive layer. The present inventors have studied the FPD described in Patent Literature 1 using a columnar crystal group containing CsI (refractive index=1.74) as the phosphor layer and a layer containing an acrylic resin (refractive index=1.45) as the adhesive layer. As a result, it was found that light generated from columnar crystals contained in the phosphor layer is difficult to reflect at the interface between the phosphor layer and the adjacent adhesive layer and leaks easily into the adhesive layer. The term "total reflection", as used herein, refers to a phenomenon that is more likely to occur as the refractive index difference between two media increases. Due to a small refractive index difference between the phosphor layer and the adjacent adhesive layer, the "total reflection" may be less likely to occur at the interface between the phosphor layer and the adhesive layer. Thus, the present inventors have arranged a low-refractive-index layer with a lower refractive index than the adhesive layer between the phosphor layer ("scintillator" in the present disclosure) and the adhesive layer.

Due to a larger refractive index difference between the scintillator and the low-refractive-index layer than between the scintillator and the adhesive layer, light from the scintillator is more likely to be reflected at the interface between the scintillator and the low-refractive-index layer. This makes it difficult for light to leak from the scintillator into the adhesive layer. Consequently, a radiation detector including such a scintillator unit has improved sensitivity to radiation. Furthermore, light generated from the scintillator is difficult to propagate and diffuse in the adhesive layer. This also improves the resolution of an image to be formed.

Embodiments of the present disclosure are described in detail below. Unless otherwise specified, physical properties are determined at 25° C.

Figure 1A:
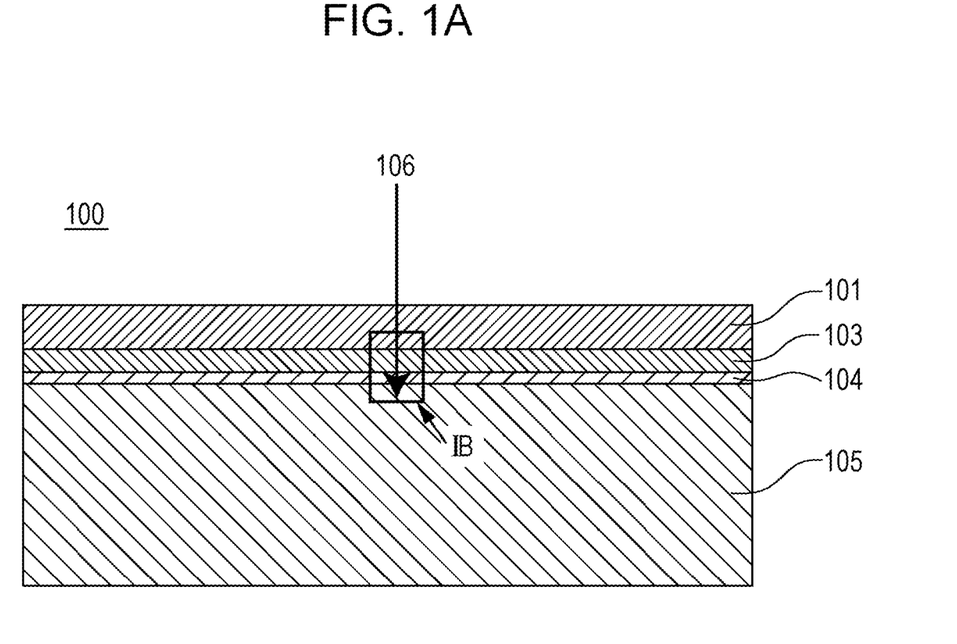
FIG. 1A is a schematic cross-sectional view of an embodiment of a scintillator unit according to the present disclosure.
Figure 1B:
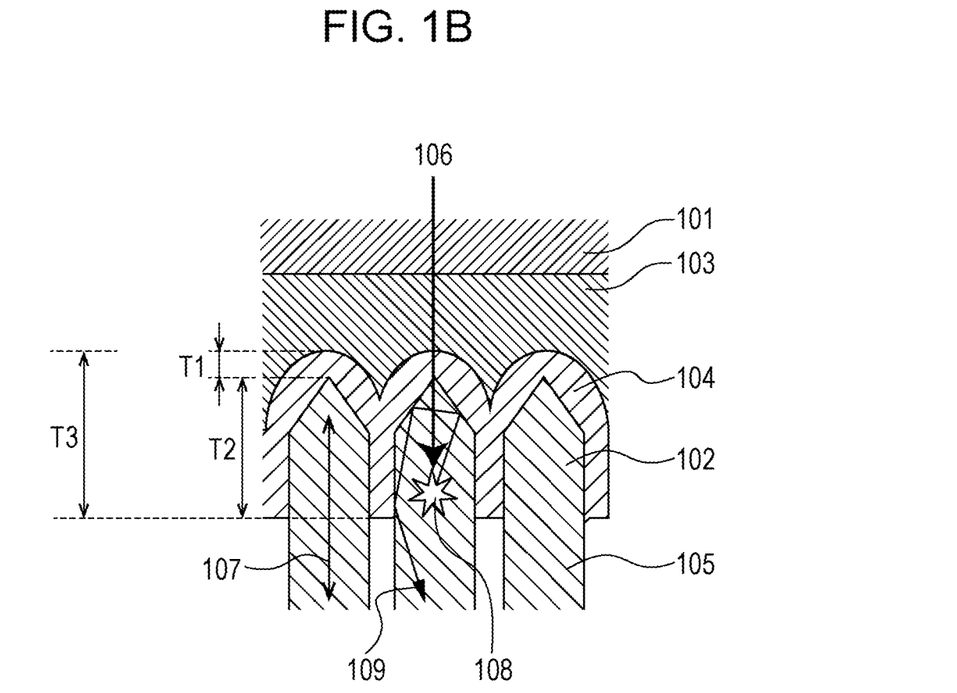
FIG. 1B is a schematic enlarged cross-sectional view of an embodiment of a scintillator unit according to the present disclosure.

FIG. 1A is a schematic cross-sectional view of an embodiment of a scintillator unit according to the present disclosure, and FIG. 1B is an enlarged view of the schematic cross-sectional view. In FIG. 1A, a scintillator unit 100 includes a low-refractive-index layer 104, an adhesive layer 103, and a supporting member 101 in this order on a scintillator 105. The incident direction of radiation 106 on the scintillator unit 100 is indicated by an arrow. The components of the scintillator unit 100 are described in detail below.

[Scintillator 105]

FIG. 1B is an enlarged view of a square region of FIG. 1A. Preferably, the scintillator 105 in the scintillator unit 100 according to the present disclosure contains a material that emits light by radiation (X-rays, γ radiation, charged particles, or the like) and is an aggregate of a plurality of crystals (columnar crystals) with a columnar (or acicular) shape (hereinafter referred to as a columnar crystal group). The columnar crystal group can be used as the scintillator 105 to easily guide light and prevent light scattering. This can further prevent the leakage of light into the adhesive layer, makes it difficult for light generated from a columnar crystal to enter another columnar crystal, and thereby improves the resolution of an image to be formed.

The scintillator unit 100 according to the present disclosure is particularly suitable for a radiation detector produced by a method of directly forming a film of a scintillator on a sensor panel including a detecting unit. In such a case, the scintillator 105 may be referred to as a scintillator film.

As illustrated in FIG. 1B, a central axis 107 of a columnar crystal 102 is preferably arranged in parallel with the incident direction of the radiation 106. However, it is not necessary to be strictly parallel to the incident direction of the radiation 106, and the allowable inclination is preferably within 10 degrees, more preferably within 5 degrees. Furthermore, the columnar crystal 102 is not necessarily uniformly inclined. The lack of strict parallelism does not significantly affect the advantages of the present disclosure. Scintillation light 109 emitted from the scintillator 105 by the radiation 106 is repeatedly reflected and propagated in the columnar crystal 102.

The columnar crystal group does not necessarily have the same columnar crystal diameter and may be an aggregate of columnar crystals with different diameters. The columnar crystal diameter refers to an equivalent circular diameter in a cross section perpendicular to the central axis of the columnar crystal. The term "equivalent circular diameter", as used herein, refers to a "projected area equivalent circular diameter" generally referred to in microscopy and refers to the diameter of a perfect circle with the same area as the projected area. The columnar crystal diameter preferably ranges from 0.01 to 50 μm, more preferably 0.1 to 15 μm. The columnar crystal diameter may vary in the range of 0.01 to 50 μm from one end to the other end.

A columnar crystal diameter of less than 0.01 μm is considerably smaller than the wavelength of light and results in suppressed geometrical optical diffraction and optical scattering. Thus, light passes the boundary of the side surface of each columnar crystal and propagates widely into the columnar crystal group, which can be responsible for lower resolution. A columnar crystal diameter of more than 50 μm results in an increased amount of light that is not totally reflected by the side surface of the columnar crystal and may result in leakage of a large amount of light into a columnar crystal adjacent to the original columnar crystal.

The columnar crystals 102 preferably have the same length in the direction of the central axis 107. A columnar crystal group with more uniform lengths tends to result in higher resolution. However, the columnar crystals does not necessarily have the same length, and the scintillator 105 may contain long and short columnar crystals. For example, scintillation light leaking from a short columnar crystal can enter an adjacent columnar crystal and travel in the columnar crystal scintillator toward a light-receiving device directly under the adjacent columnar crystal. Thus, the scintillator 105 may have any columnar crystal structure that can achieve required resolution.

The scintillator 105 may include a space or a light scattering body in the columnar crystals 102. Although such a space or light scattering body scatters scintillation light, scattered light can enter an adjacent columnar crystal and can be guided in the columnar crystal toward a light-receiving device directly under the adjacent columnar crystal.

Examples of materials applicable to the scintillator 105 include halides of alkali metals, alkaline-earth metals, transition metals, typical elements, and rare-earth metals. Additional examples include oxides, nitrides, chalcogenides, and group 13 and 14 compounds. Specific examples include Tl-doped NaI, Tl-doped CsI, Na-doped CsI, $Lu_2SiO_5$, Ce-doped $Lu_2Y_2SiO_5$, $Gd_2SiO_5$, $Bi_4Ge_3O_{12}$, $ZnWO_4$, $CdWO_4$, $PbWO_4$, $LuAlO_3$, Ce-doped $Y_3Al_5O_{12}$, Ce-doped $YAlO_3$, Ce-doped $Lu_3Al_5O_{12}$, Pr-doped $Lu_3Al_5O_{12}$, and $CeF_3$. In particular, the scintillator 105 preferably contains Tl-doped CsI.

[Supporting Member 101]

Approximately half of the light generated by the scintillator 105 is repeatedly reflected in the columnar crystal 102 and travels toward a surface of the scintillator 105 (hereinafter referred to as a light extraction surface) opposite the surface of the scintillator 105 on which the supporting member 101 and the adhesive layer 103 are located, and the other approximately half of the light may travel toward the supporting member 101. Due to the low-refractive-index layer 104 with a lower refractive index than the adhesive layer 103 between the adhesive layer 103 and the scintillator 105, most of the light transmitted in the direction of the supporting member 101 is reflected at the interface between the columnar crystal 102 and the low-refractive-index layer 104 and is guided to the light extraction surface.

At least part of the supporting member 101 preferably includes a reflective layer or a light-absorbing layer. When the supporting member 101 includes a reflective layer that can reflect light, light leaking into the adhesive layer can be reflected back into the scintillator and travel toward the light extraction surface, thus increasing the amount of light to be detected and improving sensitivity to radiation.

The reflective layer may be formed of a metal material, such as aluminum. The reflective layer is preferably a dielectric multilayer reflective layer with higher reflectance than metal materials. This further improves the sensitivity to radiation. The low-refractive-index layer 104 and the reflective layer are located on the scintillator 105. The low-refractive-index layer 104 and the reflective layer are bonded together via the adhesive layer 103. The adhesive layer 103 may also be referred to as a space-filling layer.

When the supporting member 101 includes a light-absorbing layer that can absorb light, the light-absorbing layer can absorb light leaking into the adhesive layer 103 and can prevent scintillation light emitted from a columnar crystal from entering another columnar crystal. The light-absorbing layer may absorb part or all of the light. The use of the light-absorbing layer decreases the sensitivity to radiation but improves the resolution of an image to be formed. The light-absorbing layer may be a sheet containing carbon particles.

The scintillator unit preferably includes the low-refractive-index layer between end portions of the columnar crystals in the extending direction and the adhesive layer. The low-refractive-index layer 104 on one surface of the scintillator 105 (columnar crystal group) improves the total reflection efficiency of light at the interface between the columnar crystal 102 and the low-refractive-index layer 104 and prevents light from leaking from the scintillator into the adhesive layer 103.

In the structure of the present disclosure illustrated in FIGS. 1A and 1B, the scintillator 105, the low-refractive-index layer 104, and the adhesive layer 103 are arranged in this order. It is important to form the low-refractive-index layer 104 in contact with the scintillator 105 between the scintillator 105 and the adhesive layer 103. This can greatly decrease the amount of light leaking from the columnar crystal 102 into the adhesive layer 103.

A scintillator unit including a CsI (n=1.74) columnar film as the scintillator 105 is described below. A low-refractive-index layer (n=1.15) on the upper surface of the CsI can improve the total reflection efficiency at the interface between the low-refractive-index layer and the CsI and can hold a large amount of light within the CsI. Consequently, the radiation detector including the scintillator unit can have improved sensitivity to radiation and improved resolution of an image to be formed. That is, it is assumed that the radiation 106 enters the scintillator 105 and is converted into visible light at a luminous point 108. Out of the generated light, the scintillation light 109 reaching the interface between the scintillator 105 and the low-refractive-index layer 104 is more likely to remain in the scintillator 105 due to total reflection.

The total reflection efficiency at the interface with CsI (n=1.74) is compared between a known structure in which an adhesive layer (n=1.45) containing an acrylic resin is in contact with the CsI and a structure of the present disclosure in which the low-refractive-index layer 104 is in contact with the CsI. The total reflection efficiency was calculated using Snell's law for the solid angle of light emitted from the upper surface of the CsI. The ratio S of light entering a medium on the upper surface of the CsI from one point on the upper surface without total reflection to the light entering the medium from the point is represented by $S=1-\cos[\arcsin(n/1.74)]$. When the medium on the upper surface has a refractive index of 1.74, due to no refractive index difference, all the light is transmitted and S=1. If the medium on the upper surface has a refractive index n of 1.45, 1.20, 1.15, or 1.10, then S is 0.45, 0.28, 0.25, or 0.23, respectively. Thus, when the adhesive layer (n=1.45) is a low-refractive-index layer, the ratio of light leaking from the CsI decreases by 38% for the low-refractive-index layer with a refractive index n of 1.20, 44% for n=1.15, and 49% for n=1.10.

[Adhesive Layer 103]

The adhesive layer 103 may be formed of any material that has a function of bonding the supporting member 101 and the low-refractive-index layer 104 together. The adhesive layer 103 may be formed of a general-purpose thermoplastic resin. An acrylic resin is preferred in terms of transparency.

Figure 2A:
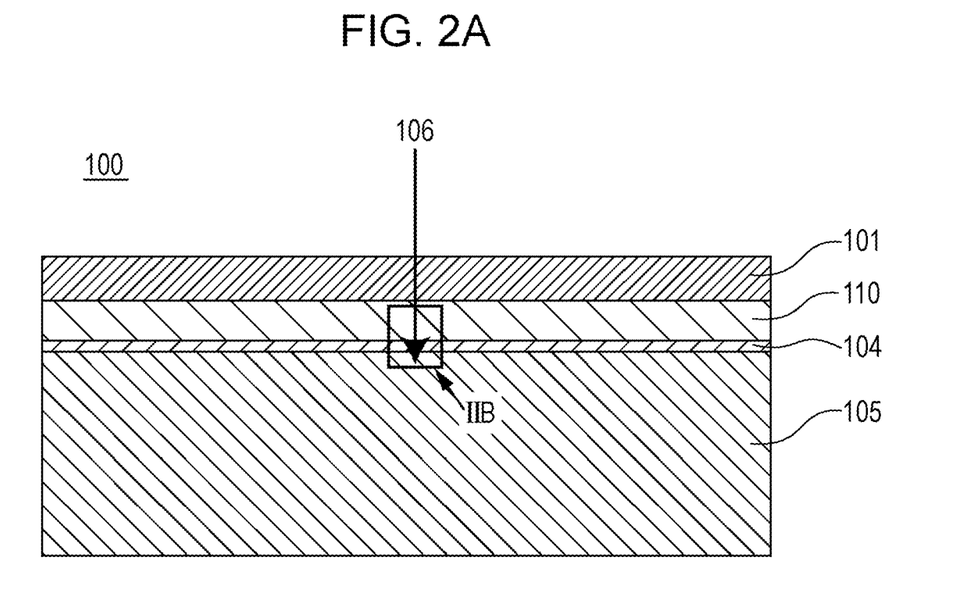
FIG. 2A is a schematic cross-sectional view of an embodiment of a scintillator unit according to the present disclosure.
Figure 2B:
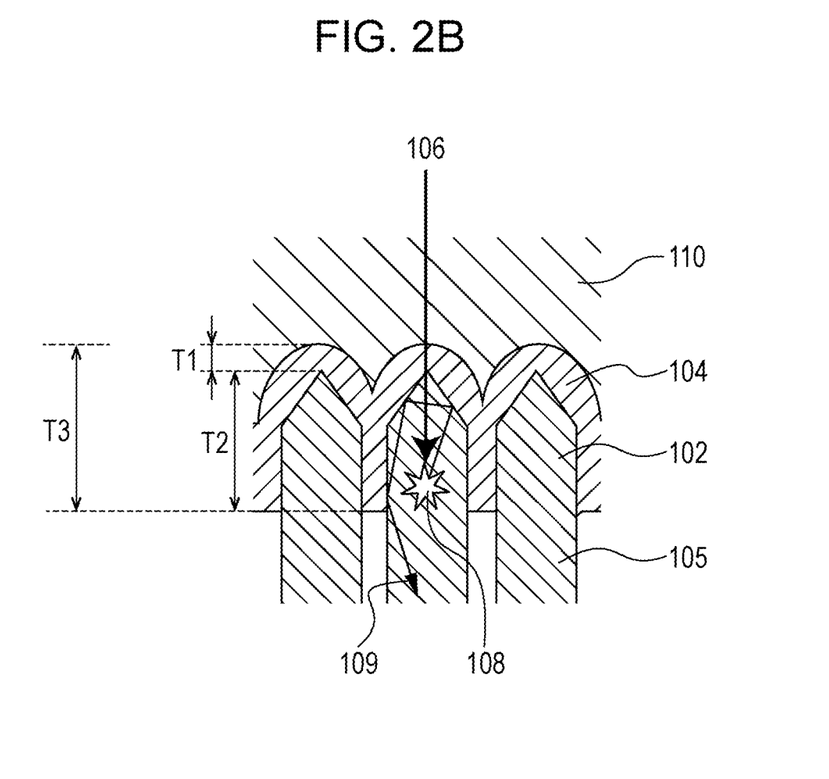
FIG. 2B is a schematic enlarged cross-sectional view of an embodiment of a scintillator unit according to the present disclosure.

Alternatively, as illustrated in FIGS. 2A and 2B, an adhesive layer 110 with functions of adhesion and reflection may also be used. The adhesive layer 110 may include a scattering layer containing light-scattering particles and a binder resin. In such a structure, the adhesive layer 110 has a role of not only bonding the supporting member and the low-refractive-index layer together but also reflecting light leaking from the low-refractive-index layer. The adhesive layer 110 preferably contains titanium oxide as the light-scattering particles and an epoxy resin as the binder, for example. In such a structure, the low-refractive-index layer 104, the adhesive layer 110 with the functions of adhesion and reflection, and the supporting member 101 are provided on the scintillator 105. When the adhesive layer 110 is used, the supporting member preferably includes a light-absorbing layer.

[Low-Refractive-Index Layer 104]

In the structures according to the present disclosure illustrated in FIGS. 1A, 1B, 2A, and 2B, the low-refractive-index layer 104 preferably has a thickness T1 in the range of 300 nm to 5 μm. In the present disclosure, the thickness T1 of the low-refractive-index layer is defined as the average distance from end portions of the columnar crystals to the interface between the low-refractive-index layer and the adhesive layer. To sufficiently increase the total reflection efficiency, it is preferable to have a thickness equal to or greater than the emission wavelength of the scintillator. This determines the lower limit of T1. When a scintillator that emits light in the visible light region is used, T1 is preferably 300 nm or more. An excessively large T1 may result in a long optical path length to the interface with the adhesive layer, easier diffusion in the transverse direction, and a decrease in resolution. Thus, T1 is preferably 5 μm or less. The penetration depth T2 in the gap between the columnar crystals of the low-refractive-index layer is preferably 25 μm or less. The penetration depth T2 in the gap between the columnar crystals of the low-refractive-index layer is a length obtained by subtracting T1 from the average distance T3 from the interface between the low-refractive-index layer and a non-low-refractive-index layer portion located between the columnar crystals to the interface between the low-refractive-index layer and the adhesive layer. An excessively large penetration depth may result in an increased ratio of light propagating between the columnar crystals and a decrease in resolution.

<Composition and Structure>

Figure 3:
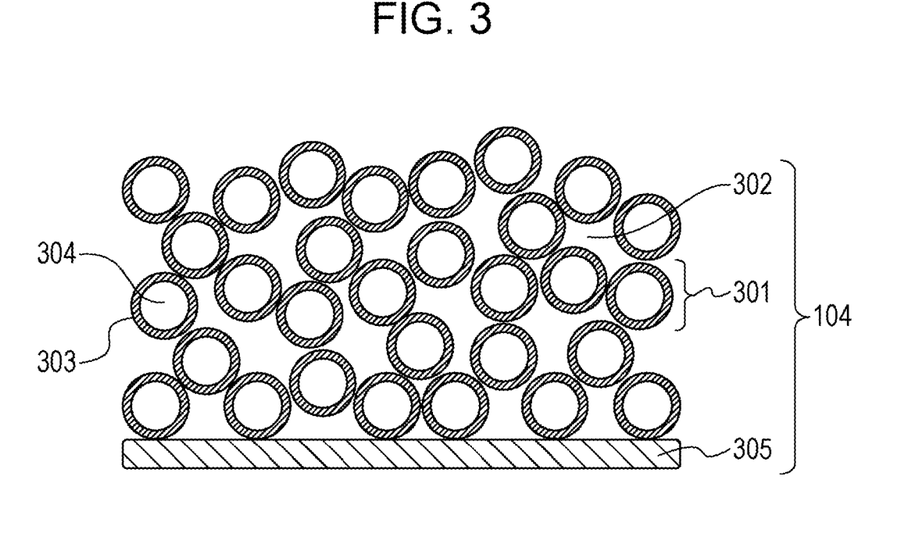
FIG. 3 is a schematic cross-sectional view of an embodiment of a low-refractive-index layer.

In FIG. 3, the strength of the low-refractive-index layer 104 can be improved by using a solid material with a refractive index of 1.65 or less as a skeleton to appropriately set the porosity for a lower refractive index.

The solid material may be crystalline or amorphous. The solid material may be particles. The particles may be, but are not limited to, spherical particles, irregular-shaped particles, the spherical or irregular-shaped particles linked in a beaded or branched chain shape, hollow particles with a cavity, or hollow particles linked in a beaded or branched chain shape.

Examples of the solid material include resins, such as fluorinated polymers and acrylic resins, fluorides, such as magnesium fluoride and calcium fluoride, carbonates, such as calcium carbonate and potassium carbonate, sulfates, such as barium sulfate, and oxides, such as silicon dioxide (hereinafter also referred to as silica) and aluminum oxide.

Examples of the solid material with a low refractive index include organic materials such as fluorinated polymers and inorganic materials such as magnesium fluoride and silicon dioxide.

However, even fluorinated polymers with a low refractive index have a refractive index of approximately 1.30, and magnesium fluoride and silicon dioxide (quartz) have a refractive index of 1.38 and 1.46, respectively, and a simple material with a refractive index much lower than 1.30 is mainly a gas such as nitrogen or oxygen.

The solid material preferably contains silicon dioxide in terms of refractive index, cost, and chemical stability. More specifically, the solid material is preferably composed mainly of silicon dioxide. The phrase "the solid material is composed mainly of silicon dioxide", as used herein, means that the silicon dioxide content of the solid material is 50% or more by mass. The silicon dioxide content of the solid material is typically 90% or more by mass.

Specific examples of silicon dioxide particles include a Snowtex series manufactured by Nissan Chemical Industries, Ltd., organosilica sol, a Thrulya series manufactured by JGC Catalysts and Chemicals Ltd., and an Aerosil series manufactured by Evonik Industries AG. and sold by Nippon Aerosil Co., Ltd.

A composite material C composed of a material A with a refractive index $n_a$ and a material B with a refractive index $n_b$ typically has a refractive index $n_c$ approximately represented by the formula (1):

Formula (1)

$$n_c = [n_a \times v_a / 100] + [n_b \times v_b / 100] \quad (1)$$

wherein $v_a$ and $v_b$ denote the volume fractions of the material A and the material B, respectively, constituting the composite material ($v_a + v_b = 100$).

According to the formula (1), a composite material of a solid material and air, that is, a porous film with a skeleton of the solid material used as the low-refractive-index layer 104 can have a lower refractive index than the original solid material. In such a structure, the solid material skeleton with a lower refractive index or the low-refractive-index layer 104 with higher porosity results in the low-refractive-index layer 104 with a lower refractive index. To increase the porosity of the low-refractive-index layer 104, the low-refractive-index layer 104 may have a porous structure. In this respect, the low-refractive-index layer 104 can be referred to as a porous film.

In the formula (1), when the material A is air and the material B is silicon dioxide, the refractive index $n_a$ of the air is 1.00, the refractive index $n_b$ of the silicon dioxide is 1.46, and the volume fraction $v_b$ of the silicon dioxide is $100-v_a$. Thus, $v_a$ can be determined as a function of the refractive index $n_c$ of the low-refractive-index layer 104. The $v_a$ refers to porosity.

The low-refractive-index layer 104 preferably has a porosity in the range of 60.0% to 95.0%, more preferably 65.0% to 90.0%.

For example, according to the formula (1), when the low-refractive-index layer 104 with a silicon dioxide (refractive index 1.46) skeleton has a porosity of less than 60.0%, the refractive index may exceed 1.15.

On the other hand, a porosity of more than 95.0% may result in the low-refractive-index layer 104 with an excessively low refractive index of less than 1.05 and low strength due to a small amount of skeleton constituting the low-refractive-index layer 104.

The silicon dioxide preferably has at least one of an organic group and a hydroxy group on its surface. Silicon dioxide with a hydroxy group on its surface has high hydrophilicity. Thus, the low-refractive-index layer 104 with a skeleton of such silicon dioxide particles can have high hydrophilicity.

For example, the surface of silicon dioxide can be modified with a silane coupling agent to impart functionality to the low-refractive-index layer 104. For silicon dioxide with a hydroxy group on its surface, a dehydration condensation reaction between the hydroxy group and a hydrolysate of a silane coupling agent can be utilized.

Examples of the organic group include alkyl groups having 1 to 4 carbon atoms, such as a methyl group, an ethyl group, a propyl group, and a butyl group; hydrocarbon groups with a polymerizable moiety, such as a vinyl group, an acrylic group, and a methacrylic group; and aromatic hydrocarbon groups, such as a phenyl group.

Silicon dioxide with an organic group on its surface can impart various functions, such as water repellency, oil repellency, biocompatibility, electron-transport characteristics, and polymerizability, to the low-refractive-index layer 104.

All of the functional groups on the surface of silicon dioxide are not necessarily substituted with an organic group, and an organic group and a hydroxy group may be present in any ratio.

[Hollow Particles]

The low-refractive-index layer 104 containing hollow particles is further described. However, the present disclosure is not limited thereto. The hollow particles have an outer shell formed of a solid material and have a cavity (space) inside the outer shell.

The low-refractive-index layer 104 preferably contains a plurality of hollow particles. The low-refractive-index layer 104 containing a plurality of hollow particles may contain solid particles or a binder in addition to the hollow particles.

FIG. 3 shows an example of the structure of the low-refractive-index layer 104 containing hollow particles as primary particles composed of a solid material.

The low-refractive-index layer 104 contains a plurality of hollow particles 301 and a space 302 between the hollow particles 301. The hollow particles also include a space 304. In FIG. 3, the reference numeral 303 denotes the outer shell, and the reference numeral 305 denotes a base material. The base material 305 is a material on which the low-refractive-index layer 104 is to be formed. In the structures according to the present disclosure illustrated in FIGS. 1A, 1B, 2A, 2B, and 4, the base material 305 corresponds to the scintillator 105.

The porosity X (%), which is the ratio of the total volume of the spaces in the hollow particles to the unit volume of the low-refractive-index layer 104, and the porosity Y (%), which is the ratio of the total volume of the space between the hollow particles to the unit volume of the low-refractive-index layer 104, preferably satisfy the relationship X<Y. (X+Y) represents the porosity of the low-refractive-index layer 104.

The refractive index n of the low-refractive-index layer 104 is represented by the following formula (2):

Formula (2)

$$n = [n_a \times (X+Y)/100] + [n_s \times (100-X-Y)/100] \quad (2)$$

wherein $n_a$ denotes the refractive index of air ($n_a$=1), and $n_s$ denotes the refractive index of the outer shell of the hollow particles ($n_s$>1). According to the formula (2), n decreases with increasing X+Y or decreasing $n_s$.

The refractive index n of the low-refractive-index layer 104 is also represented by the following formula (3):

Formula (3)

$$n = [n_a \times Y/100] + [n_p \times (100-Y)/100] \quad (3)$$

wherein $n_p$ denotes the refractive index of one hollow particle ($n_p$>1). The refractive index $n_p$ is an apparent refractive index calculated from the ratio of the volume and refractive index of the outer shell to the volume and refractive index of the space in one hollow particle. Thus, if $n_a$=1, $n_b$=$n_s$, $v_a$ denotes the volume of the space of the hollow particle, and $v_b$ denotes the volume of the outer shell in the formula (1), then $n_c$=$n_p$. According to the formula (3), n decreases with increasing Y or decreasing $n_p$.

X and Y can also be estimated by measuring the refractive index n of the low-refractive-index layer 104 by optical measurement and substituting known $n_a$, $n_s$, and $n_p$ into the formulae (2) and (3).

A dense arrangement of hollow particles decreases the volume fraction of the space between the hollow particles and increases the volume fraction of the outer shell formed of a component with a higher refractive index than air, thus increasing the refractive index of the low-refractive-index layer 104. By contrast, a sparse arrangement of hollow particles increases the volume fraction of the space between the hollow particles and decreases the volume fraction of the outer shell, thus decreasing the refractive index of the low-refractive-index layer 104. Thus, to further decrease the refractive index of the low-refractive-index layer 104, Y/X is preferably increased. More specifically, the relationship of Y/X>1, that is, X<Y is preferably satisfied.

X and Y preferably satisfy the relationship of X<(100−X−Y)<Y.

The low-refractive-index layer 104 may contain particles composed of a solid material and a binder that binds the particles together for reinforcement. When a binder is used, the solid in the low-refractive-index layer 104 is the outer shell of the hollow particles and the binder, and the volume fraction of the solid relative to the unit volume of the low-refractive-index layer 104 is represented by (100−X−Y) (%).

Satisfying the relationship of X<(100−X−Y) further improves the strength of the low-refractive-index layer 104. Satisfying the relationship of (100−X−Y)<Y further decreases the refractive index of the low-refractive-index layer 104.

The total (X+Y) of X and Y preferably ranges from 60.0% to 95.0%, more preferably 65.0% to 90.0%. (X+Y) in these ranges makes it easy to adjust the strength of the low-refractive-index layer 104 and the refractive index of the low-refractive-index layer 104 in a desired range.

In the low-refractive-index layer 104, X preferably ranges from 8.0% to 32.0%, more preferably 10.0% to 28.0%, still more preferably 12.0% to 24.0%.

On the other hand, Y preferably ranges from 30.0% to 80.0%, more preferably 35.0% to 75.0%, still more preferably 40.0% to 70.0%.

X and Y in these ranges makes it easy to adjust the strength of the low-refractive-index layer 104 and the refractive index of the low-refractive-index layer 104 in a desired range.

Although the hollow particles are substantially spherical in the example illustrated in FIG. 3, the hollow particles may have any shape. The hollow particles have the outer shell 303 and the space 304 surrounded by the outer shell and formed inside the hollow particles. In this case, the hollow particles can be considered to be core-shell particles containing air as the core.

The refractive index $n_p$ of one hollow particle is represented by the formula (4):

Formula (4)

$$n_p = [n_s \times (100-V_a)/100] + [n_a \times V_a/100] \quad (4)$$

wherein $V_a$ denotes the volume fraction of the internal space relative to the total volume of the hollow particle. Thus, the refractive index $n_p$ of one hollow particle is determined by the refractive index $n_s$ of the outer shell material and the porosity $V_a$ of the hollow particle.

The porosity $V_a$ of one hollow particle preferably ranges from 30.0% to 70.0%, more preferably 35.0% to 65.0%.

A porosity $V_a$ in these ranges can result in the low-refractive-index layer 104 with an easily lowered refractive index, the hollow particles with the outer shell of constant strength, and the low-refractive-index layer 104 of constant strength.

Like the refractive index of the solid material, the refractive index $n_s$ of the outer shell of the hollow particles is preferably 1.10 or more, 1.20 or more, 1.25 or more, 1.30 or more, or 1.35 or more, and preferably 1.65 or less or 1.60 or less. These ranges can be freely combined.

A refractive index $n_s$ of the outer shell of the hollow particles in these ranges can result in the ease of production of the low-refractive-index layer 104, the hollow particles with high strength, the low-refractive-index layer 104 with high strength, and the low-refractive-index layer 104 with a low refractive index.

The outer shell of the hollow particles may be formed of the same material as the solid material.

The outer shell of the hollow particles may have micropores. The micropores in the outer shell can further decrease the refractive index of the outer shell.

The primary particles of the hollow particles preferably have a number-average particle size in the range of 1 to 200 nm, more preferably 5 to 100 nm, still more preferably 10 to 100 nm, particularly preferably 20 to 100 nm.

A number-average particle size in these ranges can result in the ease of production of the hollow particles, easily prevented light scattering, and the low-refractive-index layer 104 with further improved transmissivity.

[Fumed Silica Particles and Chain Silica Particles]

The low-refractive-index layer 104 preferably contains at least one type of particles selected from the group consisting of secondary particles in which primary particles composed of a solid material form a three-dimensional structure, chain secondary particles in which primary particles composed of a solid material are linked in a chain, and branched chain secondary particles in which primary particles composed of a solid material are linked in a branched chain. When particles composed of a solid material form an aggregate, the aggregate is also included in the secondary particles in which primary particles composed of a solid material form a three-dimensional structure.

The secondary particles in which primary particles composed of a solid material form a three-dimensional structure, the chain secondary particles in which primary particles composed of a solid material are linked in a chain, and the branched chain secondary particles in which primary particles composed of a solid material are linked in a branched chain decrease the volume fraction of the solid material in the low-refractive-index layer 104. This can increase the volume fraction of the space. This can therefore decrease the refractive index of the low-refractive-index layer 104.

The primary particles composed of a solid material preferably has a number-average particle size in the range of 1 to 200 nm, more preferably 5 to 100 nm. The primary particles composed of a solid material still more preferably has a number-average particle size in the range of 10 to 100 nm, particularly preferably 20 to 100 nm.

When the primary particles have a number-average particle size in these ranges, it is possible to appropriately control the aggregation of particles and improve dispersibility in a coating liquid. Furthermore, it is possible to prevent the primary particles from becoming light scatterers in the wavelength range of 400 to 700 nm and further improve the transmissivity of the low-refractive-index layer 104.

Fumed silica particles are described below as an example of the secondary particles in which primary particles composed of a solid material form a three-dimensional structure. However, the present disclosure is not limited thereto.

Fumed silica particles can be produced by high-temperature hydrolysis of silicon tetrachloride in oxygen and hydrogen flame. In fumed silica particles produced by this production method, primary particles of tens of nanometers are fused to form secondary particles with a three-dimensional structure. The secondary particles may aggregate and have a complex higher-order structure.

Due to their characteristic structure, fumed silica particles are very bulky particles with an apparent specific gravity in the range of 0.01 to 0.1 $g/cm^3$. Thus, the low-refractive-index layer 104 containing the fumed silica particles has a high porosity and can significantly decrease the refractive index.

The secondary particles preferably have a number-average particle size in the range of 10 to 1000 nm, more preferably 50 to 500 nm.

When the secondary particles have a number-average particle size in these ranges, for example, primary particles of silicon dioxide form a three-dimensional structure, and the secondary particles do not have a simple structure of aggregated primary particles.

The secondary particles with the above structure make it easy to control the porosity and the refractive index of the low-refractive-index layer 104 in the above ranges. Furthermore, this makes it difficult to form a huge space, which can be a light scatterer in the wavelength range of 400 to 700 nm, between the secondary particles, and makes it easy to control the light transmittance of the low-refractive-index layer 104.

The number-average particle size of the primary particles and the secondary particles can be determined with a transmission electron microscope (TEM) (both are calculated from the arithmetic mean of the maximum diameters). The number-average particle size of the primary particles and the secondary particles can be controlled, for example, by adjusting the conditions for the high-temperature hydrolysis of silicon tetrachloride in oxygen and hydrogen flame, as described above.

<Film-Forming Method>

[Method for Preparing Coating Liquid]

A method for preparing a coating liquid for forming the low-refractive-index layer 104 is described below. Although fumed silica particles in which primary particles of silicon dioxide form a three-dimensional structure are described below, the present disclosure is not limited thereto.

Fumed silica particles are dispersed in a solvent. The solvent in which fumed silica particles are to be dispersed is preferably a solvent with a high affinity for the fumed silica particles. One solvent or a mixture of two or more solvents may be used depending on the type of functional group on the surface of the fumed silica particles.

The solvent is preferably an organic solvent and may be an alcohol solvent, such as methanol, ethanol, propanol, or isopropanol, a glycol solvent, such as ethylene glycol or propylene glycol, an ether solvent, such as dimethyl ether, diethyl ether, ethylene glycol monomethyl ether, ethylene glycol monoethyl ether, propylene glycol monomethyl ether, or propylene glycol monoethyl ether, an acetate solvent, such as ethyl acetate, propyl acetate, propylene glycol monomethyl ether acetate, or propylene glycol monoethyl ether acetate, or a ketone solvent, such as acetone or methyl ethyl ketone.

Although the solvent may be water, water has a high surface tension, causes a large capillary force when dried, and sometimes shrinks the space between the fumed silica particles. This is likely to decrease the porosity of the low-refractive-index layer 104 and can increase the refractive index.

When an alkali metal, particularly CsI, is used as a material of the scintillator 105, water is not appropriate for the solvent due to its strong deliquescence. Particles composed of a solid material may be used alone or in combination of two or more types thereof.

The amount of particles composed of a solid material in the coating liquid is preferably 1.0% or more by mass, more preferably 2.0% or more by mass, still more preferably 3.0% or more by mass, particularly preferably 7.0% or more by mass. The amount of silica particles in the coating liquid is preferably 50.0% or less by mass, more preferably 30.0% or less by mass, still more preferably 20.0% or less by mass. These ranges can be freely combined.

For example, the concentration of the fumed silica particles (solid content) in the coating liquid preferably ranges from 1.0% to 30.0% by mass, more preferably 2.0% to 20.0% by mass.

When the amount of particles composed of a solid material in the coating liquid, for example, the amount (concentration) of fumed silica particles is in the above ranges, the thickness of the low-refractive-index layer 104 is easily adjusted to 500 nm or more. This can also improve the uniform dispersibility of the fumed silica particles in the solvent and makes it easy to adjust the transmissivity of the low-refractive-index layer 104 in the above ranges.

Fumed silica particles are added to the solvent and are dispersed. When a coating liquid in which fumed silica particles are dispersed while maintaining a complex higher-order structure is formed into a film, the fumed silica particles and the space between the fumed silica particles have such a size that visible light is scattered, and therefore the transmissivity of the low-refractive-index layer 104 may decrease. When fumed silica particles are subjected to dispersion treatment, the transparency of the coating liquid increases with the dispersion treatment time.

When a coating liquid containing appropriately dispersed fumed silica particles is formed into a film, the skeleton of the fumed silica particles and the space between the fumed silica particles have such a size that they do not become scatterers of visible light. Thus, the low-refractive-index layer 104 has high transmissivity.

Further dispersion treatment is likely to destroy the bulky higher-order structure of the fumed silica particles into primary particles, may decrease the porosity, and tends to increase the refractive index of the low-refractive-index layer 104.

Furthermore, excessive dispersion treatment causes the so-called overdispersion, is likely to reaggregate the fumed silica particles, and may decrease the transmissivity of the low-refractive-index layer 104 after film formation.

Thus, an appropriate dispersion state is preferred. A stirrer, ultrasonic waves, a planetary mixer, a ball mill, a bead mill, a homogenizer, or the like can be used for the dispersion treatment.

Although hollow particles with a silicon dioxide outer shell are used as a solid material in the following example, the present disclosure is not limited to this example.

A dispersion liquid of hollow particles can be used. The dispersion liquid of hollow particles may be any dispersion liquid of hollow particles that satisfies the porosity of the hollow particles, the refractive index of the outer shell of the hollow particles, the number-average particle size of the primary particles of the hollow particles, and the like.

For example, the Thrulya series manufactured by JGC Catalysts and Chemicals Ltd., which is an isopropanol (hereinafter also referred to as IPA) dispersion liquid of hollow particles with a silicon dioxide outer shell (hereinafter also referred to as hollow silica particles), is preferably used. In addition to commercial products, such as the Thrulya series, hollow silica particles dispersed in a solvent by the same method as the solvent dispersion of the fumed silica particles may be used.

The concentration of hollow particles in a solvent may be in the same range as the concentration of the fumed silica particles (solid content) in the coating liquid.

The surface of hollow silica particles has a hydroxy group and is hydrophilic. Thus, highly hydrophobic solvents are not suitable. More specifically, an organic solvent with an octanol/water partition coefficient log $P_{ow}$ of 2 or less is preferably used. The organic solvent may be an alcohol solvent, such as methanol, ethanol, propanol, or isopropanol, a glycol solvent, such as ethylene glycol or propylene glycol, an ether solvent, such as dimethyl ether, diethyl ether, ethylene glycol monomethyl ether, ethylene glycol monoethyl ether, propylene glycol monomethyl ether, or propylene glycol monoethyl ether, an acetate solvent, such as ethyl acetate, propyl acetate, propylene glycol monomethyl ether acetate, or propylene glycol monoethyl ether acetate, or a ketone solvent, such as acetone or methyl ethyl ketone.

As described above, to decrease the refractive index of the film, it is necessary to increase Y and X+Y. One method is to randomly arrange hollow silica particles.

A method of randomly arranging hollow silica particles is described below. Hollow silica particles can be randomly arranged by forming a loose aggregate of the hollow silica particles in a dispersion liquid.

Aggregates are also included in secondary particles in which primary particles composed of a solid material form a three-dimensional structure.

One method of aggregating hollow silica particles well dispersed in a dispersion liquid may be a method of adding a solvent (hereinafter referred to as an aggregating agent) with a higher log $P_{ow}$ than the dispersion medium. The aggregating method is not limited to this method and is preferably a method by which the aggregation state of hollow silica particles can be controlled.

The surface of hollow silica particles has a hydroxy group and is hydrophilic. Thus, the addition of an aggregating agent with a higher log $P_{ow}$ than the dispersion medium, that is, an aggregating agent that is more hydrophobic than the dispersion medium causes the aggregation of the hollow silica particles.

The log $P_{ow}$ and addition amount of an aggregating agent for aggregating hollow silica particles well dispersed in a dispersion liquid are described below. An excessively small difference in log $P_{ow}$ between the dispersion medium and the aggregating agent causes no aggregation of hollow silica particles. An excessively large difference in log $P_{ow}$ between the dispersion medium and the aggregating agent causes strong aggregation of the hollow silica particles even when a small amount of aggregating agent is added. When hollow silica particles form a large aggregate, the aggregate itself may become a light scatterer.

On the other hand, a large space formed between large aggregates of hollow silica particles also tends to become a light scatterer, may make the low-refractive-index layer 104 cloudy after coating, and may decrease the transmissivity.

Furthermore, significant aggregation tends to decrease the storage stability of the coating liquid. Thus, to form the low-refractive-index layer 104 with a low refractive index and high transmissivity, the aggregation state of the hollow silica particles is preferably controlled by the type and addition amount of the aggregating agent. The refractive index of the low-refractive-index layer 104 may be controlled by utilizing such properties and controlling the aggregation state of the hollow silica particles by the type and addition amount of the aggregating agent.

Furthermore, filling the space between the hollow silica particles with some material may decrease Y and X+Y and increase the refractive index of the low-refractive-index layer 104. Thus, the aggregating agent can preferably be removed and is more preferably volatilized by heating in a downstream process.

The aggregating agent may be, but is not limited to, silicone oil, such as X-22-164 (manufactured by Shin-Etsu Chemical Co., Ltd.).

A method for forming the low-refractive-index layer 104 is described below.

The coating liquid is used to form a film. The film may be formed by a bar coating method, a doctor blade method, a squeegee method, a spray method, a spin coating method, a dip coating method, or a screen printing method. Among them, the spin coating method is preferably used to make the thickness of the low-refractive-index layer 104 uniform. When the film is formed on a large-area sensor panel on which a scintillator is formed, a spray method is preferably used.

Furthermore, to form the low-refractive-index layer 104 with a desired thickness and a flat upper surface, the rotational speed in the spin coating method may be appropriately adjusted.

The film formed by such a method is preferably dried in the temperature range of 20° C. to 100° C.

The film may be further heat-treated. The heat treatment is preferably performed in the temperature range of 100° C. to 200° C., more preferably 120° C. to 180° C.

At a heating temperature to 100° C. or more, for example, the solvent is less likely to remain in the space in the hollow particles. At a heating temperature of 200° C. or less, the performance of a sensor panel corresponding to a light detecting unit 113 is less likely to deteriorate.

When the film contains a binder and a polymerization initiator, it is preferable to include a heat curing or photo-curing step. For heat curing, the solvent may be evaporated simultaneously with the heat curing of the binder in a drying or heating step.

A film formed of fine particles typically maintains its film shape by intermolecular force. Furthermore, hydrophobic interaction acts on a hydrophobic surface of fine particles, and liquid cross-linking acts on a hydrophilic surface of fine particles. These are physical interactions. When a film is heat-treated, for example, hydroxy groups on the surface of fumed silica particles are chemically bonded to each other by a dehydration reaction and can be expected to improve the strength of the film.

When a film containing the particles composed of a solid material is formed to decrease the refractive index, van der Waals forces acting between the particles and liquid cross-linking maintain the structure and the film shape.

A binder for binding particles together may be used in a method for improving the strength of a film with such a structure. From the perspective of improving the strength of the film, the low-refractive-index layer 104 may further contain a binder.

The low-refractive-index layer 104 preferably contains a bound material formed by binding a solid material with a binder. More specifically, the low-refractive-index layer 104 preferably contains a bound material formed by binding particles composed of a solid material with a binder. The binding of a solid material with a binder is a concept including any binding between primary particles composed of the solid material, between secondary particles formed by primary particles composed of the solid material, between the primary particles and the secondary particles, and the like. The binding may be chemical binding, such as an ionic bond or a covalent bond, or mechanical adhesion.

The binder may be a resin, such as acrylic resin, fluororesin, styrene resin, imide resin, urethane resin, or phenolic resin.

The binder may also be an organosilicon compound produced by polymerizing silicone oil with a polymerizable group or by hydrolysis and condensation polymerization of a silicon alkoxide.

In addition to these binders, any clear colorless binder with a low refractive index and capable of binding particles may be used.

An exemplary method for producing a film containing a binder includes the steps of preparing a liquid mixture containing a solid material, a solvent, and the binder, preparing a coating liquid by dispersion treatment of the liquid mixture, and forming a film by applying and drying the coating liquid, and if necessary by heating the coating liquid or by high-energy radiation of the coating liquid.

The binder preferably contains siloxane, more preferably silsesquioxane.

Silsesquioxane is a compound with a T3 unit structure represented by the compositional formula $[R^1(SiO_{1.5})_n]$ ($R^1$ denotes a reactive functional group, for example, at least one selected from the group consisting of polymerizable groups, a hydroxy group, a chlorine atom, alkyl groups with 1 to 6 carbon atoms, and alkoxy groups with 1 to 6 carbon atoms) and is a hybrid material of silicon oxide and an organic substance.

Silsesquioxane (hereinafter sometimes abbreviated to SQ) is a siloxane compound with the main chain backbone composed of Si—O bond and is represented by the composition formula $[R^1(SiO_{1.5})_n]$. $R^1$ preferably denotes at least one polymerizable group selected from the group consisting of an acryloyl group, a methacryloyl group, an oxetanyl group, and an epoxy group.

When silsesquioxane plays a role of binding a large number of particles composed of a solid material together, the film can have much higher strength while retaining high porosity.

Silsesquioxane may have any polymer form, for example, known linear polysiloxane, cage-like polysiloxane, or ladder-like polysiloxane. The silsesquioxane structure is a structure in which each silicon atom is bonded to three oxygen atoms and each oxygen atom is bonded to two silicon atoms (the number of oxygen atoms relative to the number of silicon atoms is 1.5). Linear polysiloxane, cage-like polysiloxane, and ladder-like polysiloxane may be mixed in terms of cost.

The silsesquioxane is preferably a compound with a polymerizable group ($R^1$ in the above formula) in the molecule and curable by radical polymerization or cationic polymerization.

Silsesquioxane curable by radical polymerization may be silsesquioxane with an acryloyl group or a methacryloyl group as R. Silsesquioxane curable by cationic polymerization may be silsesquioxane with an oxetanyl group or an epoxy group as R.

Specific examples include silsesquioxane derivatives SQ series (AC-SQ, MAC-SQ, and OX-SQ) manufactured by Toagosei Co., Ltd.

Silsesquioxane is a liquid with high viscosity and is preferably added to the coating liquid. If necessary, a polymerization initiator may be added.

The binder content of a functional film preferably ranges from 3.0 to 60.0 parts by mass, more preferably 7.0 to 30.0 parts by mass, per 100 parts by mass of particles composed of a solid material. The binder content of a functional film still more preferably ranges from 7.0 to 25.0 parts by mass, particularly preferably 10.0 to 25.0 parts by mass, per 100 parts by mass of particles composed of a solid material.

The coating liquid can be applied to a base material, and silsesquioxane can be cured by heating or photoirradiation.

In this operation, a film containing a bound material in which particles composed of a solid material are bound together with silsesquioxane is formed. Silsesquioxane can be cured to increase the strength of the film.

Examples of the polymerization initiator include radical photopolymerization initiators, cationic photopolymerization initiators, thermal radical polymerization initiators, and thermal cationic polymerization initiators. These polymerization initiators may be used alone or in combination.

Examples of the radical photopolymerization initiators include, but are not limited to, optionally substituted 2,4,5-triarylimidazole dimers, such as a 2-(o-chlorophenyl)-4,5-diphenylimidazole dimer, a 2-(o-chlorophenyl)-4,5-di (methoxyphenyl)imidazole dimer, a 2-(o-fluorophenyl)-4,5-diphenylimidazole dimer, and a 2-(o- or p-methoxyphenyl)-4,5-diphenylimidazole dimer; benzophenone derivatives, such as benzophenone, N,N'-tetramethyl-4,4'-diaminobenzophenone (Michler's ketone), N,N'-tetraethyl-4,4'-diaminobenzophenone, 4-methoxy-4'-dimethylaminobenzophenone, 4-chlorobenzophenone, 4,4'-dimethoxybenzophenone, and 4,4'-diaminobenzophenone; α-amino aromatic ketone derivatives, such as 2-benzyl-2-dimethylamino-1-(4-morpholinophenyl)-butanone-1, 2-methyl-1-[4-(methylthio)phenyl]-2-morpholino-propan-1-one; quinones, such as 2-ethylanthraquinone, phenanthrenequinone, 2-t-butylanthraquinone, octamethylanthraquinone, 1,2-benzanthraquinone, 2,3-benzanthraquinone, 2-phenylanthraquinone, 2,3-diphenylanthraquinone, 1-chloroanthraquinone, 2-methylanthraquinone, 1,4-naphthoquinone, 9,10-phenanthraquinone, 2-methyl-1,4-naphthoquinone, and 2,3-dimethylanthraquinone; benzoin ether derivatives, such as benzoin methyl ether, benzoin ethyl ether, and benzoin phenyl ether; benzoin derivatives, such as benzoin, methylbenzoin, ethylbenzoin, and propylbenzoin; benzyl derivatives, such as benzyl dimethyl ketal; acridine derivatives, such as 9-phenylacridine and 1,7-bis(9,9'-acridinyl)heptane; N-phenylglycine derivatives, such as N-phenylglycine; acetophenone derivatives, such as acetophenone, 3-methylacetophenone, acetophenone benzil ketal, 1-hydroxycyclohexyl phenyl ketone, and 2,2-dimethoxy-2-phenylacetophenone; thioxanthone derivatives, such as thioxanthone, diethylthioxanthone, 2-isopropylthioxanthone, and 2-chlorothioxanthone; acylphosphine oxide derivatives, such as 2,4,6-trimethylbenzoyldiphenylphosphine oxide, bis(2,4,6-trimethylbenzoyl)phenylphosphine oxide, and bis(2,6-dimethoxybenzoyl)-2,4,4-trimethylpentylphosphine oxide; oxime ester derivatives, such as 1,2-octanedione, 1-[4-(phenylthio)-, 2-(O-benzoyloxime)] and ethanone, 1-[9-ethyl-6-(2-methylbenzoyl)-9H-carbazol-3-yl]-, 1-(0-acetyloxime); xanthone, fluorenone, benzaldehyde, fluorene, anthraquinone, triphenylamine, carbazole, 1-(4-isopropylphenyl)-2-hydroxy-2-methylpropan-1-one, and 2-hydroxy-2-methyl-1-phenylpropan-1-one.

Examples of commercial products of the radical photopolymerization initiators include, but are not limited to, Irgacure 184, 369, 651, 500, 819, 907, 784, 2959, CGI-1700, -1750, and -1850, CG24-61, Darocur 1173, Lucirin TPO, LR8893, and LR8970 (manufactured by BASF, "Darocur" and "Lucirin" are registered trademarks), and Uvecryl P36 (manufactured by UCB).

The cationic photopolymerization initiators are preferably onium salts, aromatic onium salts, arylsulfonium salts, aryliodonium salts, and the like. Specific examples of the anion include tetrafluoroborate ion, hexafluorophosphate ion, hexafluoroantimonate ion, perchlorate ion, trifluoromethanesulfonate ion, and fluorosulfonate ion.

Examples of commercial products of the cationic photopolymerization initiators include CPI-210S (manufactured by San-Apro Ltd.), UVI-6950 (manufactured by Union Carbide Corporation), and Adeka Optomer SP-150 (manufactured by Adeka Corporation).

The polymerization initiator content of the coating liquid preferably ranges from 0.01 to 1.5 parts by mass, more preferably 0.03 to 1.0 part by mass, per 100 parts by mass of the silsesquioxane solid.

A coating liquid may be prepared by mixing particles composed of a solid material, a solvent, a binder, and an optional polymerization initiator. The solvent is preferably an organic solvent. The organic solvent may be, but is not limited to, an alcohol, a carboxylic acid, an aliphatic or alicyclic hydrocarbon, an aromatic hydrocarbon, an ester, a ketone, an ether, or a mixed solvent of two or more thereof.

Examples of the alcohol include methanol, ethanol, 2-propanol, butanol, 2-methoxyethanol, 2-ethoxyethanol, 1-methoxy-2-propanol, 1-ethoxy-2-propanol, 1-propoxy-2-propanol, 4-methyl-2-pentanol, 2-ethylbutanol, 3-methoxy-3-methylbutanol, ethylene glycol, diethylene glycol, and glycerin.

Specific examples of the carboxylic acid include n-butyric acid, α-methylbutyric acid, i-valeric acid, 2-ethylbutyric acid, 2,2-dimethylbutyric acid, 3,3-dimethylbutyric acid, 2,3-dimethylbutyric acid, 3-methylpentanoic acid, 4-methylpentanoic acid, 2-ethylpentanoic acid, 3-ethylpentanoic acid, 2,2-dimethylpentanoic acid, 3,3-dimethylpentanoic acid, 2,3-dimethylpentanoic acid, 2-ethylhexanoic acid, and 3-ethylhexanoic acid.

Specific examples of the aliphatic or alicyclic hydrocarbon include n-hexane, n-octane, cyclohexane, cyclopentane, and cyclooctane.

The aromatic hydrocarbon is preferably toluene, xylene, or ethylbenzene.

Examples of the ester include ethyl formate, ethyl acetate, n-butyl acetate, ethylene glycol monomethyl ether acetate, ethylene glycol monoethyl ether acetate, ethylene glycol monobutyl ether acetate, and γ-butyrolactone.

Examples of the ketone include acetone, methyl ethyl ketone, methyl isobutyl ketone, and cyclohexanone.

Examples of the ether include dimethoxyethane, tetrahydrofuran, dioxane, and diisopropyl ether.

To prepare the coating liquid, among the solvents described above, alcohols are preferably used in terms of solution stability.

The coating liquid can be prepared by adding a predetermined amount of binder and an optional polymerization initiator to a liquid containing particles composed of a solid material dispersed in a solvent. A liquid containing particles dispersed in an organic solvent may be prepared by dispersing a particle powder in the solvent by the same method as the above dispersion treatment (for example, with a ball mill or the like) or may be a commercial dispersion liquid.

When the coating liquid is used to form a film, the coating is performed in an inert gas atmosphere, such as dry air or dry nitrogen. The dry atmosphere preferably has a relative humidity of 30% or less.

Furthermore, a solution coating method for forming a film can be a known coating method, such as a dipping method, a spin coating method, a spray method, a printing method, a flow coating method, or a combination thereof. The film thickness can be controlled by changing the pulling speed in the dipping method or the substrate rotational speed in the spin coating method or by changing the concentration of the coating liquid.

The film may be cured by high-energy radiation, such as photoirradiation or radiation, or by heating. High-energy radiation and heating may be combined for curing.

For curing by high-energy radiation, the high-energy beam may be, but is not limited to, an electron beam, X-rays, ultraviolet radiation, or the like. When the high-energy beam is ultraviolet radiation, the radiation wavelength preferably ranges from 160 to 400 nm, and the output preferably ranges from 0.1 to 2000 mW/cm$^2$. From the perspective of preventing the oxidation of silsesquioxane, the curing atmosphere is preferably an inert atmosphere, such as nitrogen. Curing by heating may be performed in the temperature range of 50° C. to 250° C., preferably 80° C. to 200° C., for 1 to 20 minutes.

<Method for Evaluating Film Porosity and Refractive Index>

The porosity X (%) and the porosity Y (%) of the film can be calculated as described below.

First, a film formed on a base material is coated with a carbon film using a Model 681 ion beam coater IBC (manufactured by Gatan, Inc.) and is then subjected to ion beam slicing (30 kV-0.1 nA) in a focused ion beam processing apparatus (FIB-SEM, manufactured by FEI Company, Nova 600). An SEM image is then acquired with a scanning electron microscope (hereinafter referred to as an SEM) at an accelerating voltage of 2 kV.

The observation magnification of the SEM image is such that the entire film can be observed at least in the thickness direction and, for example, the shape of each hollow particle can be discriminated. More specifically, the observation magnification is approximately 50,000 to 200,000.

The unit volume of the film is 1000 nm×1000 nm×100 nm (in the thickness direction). To calculate the porosity in the cross-sectional SEM image, hollow particles and the space between the hollow particles are distinguished by binarization of a gray scale image, and the area of each region is calculated. Image processing is performed using image analysis software Image J (NIH Image, available from https://imagej.nih.gov/ij/).

More specifically, the porosity X (%) is calculated by multiplying the area A (%) of the hollow particles by the volume fraction $V_a$ of the internal space relative to the total volume of the hollow particles: $X=A\times V_a$. The porosity Y (%) is Y=100−A.

The refractive index n of the low-refractive-index layer 104 can be calculated using the formula (2) from X and Y thus calculated.

[Radiation Detector]

Figure 4:
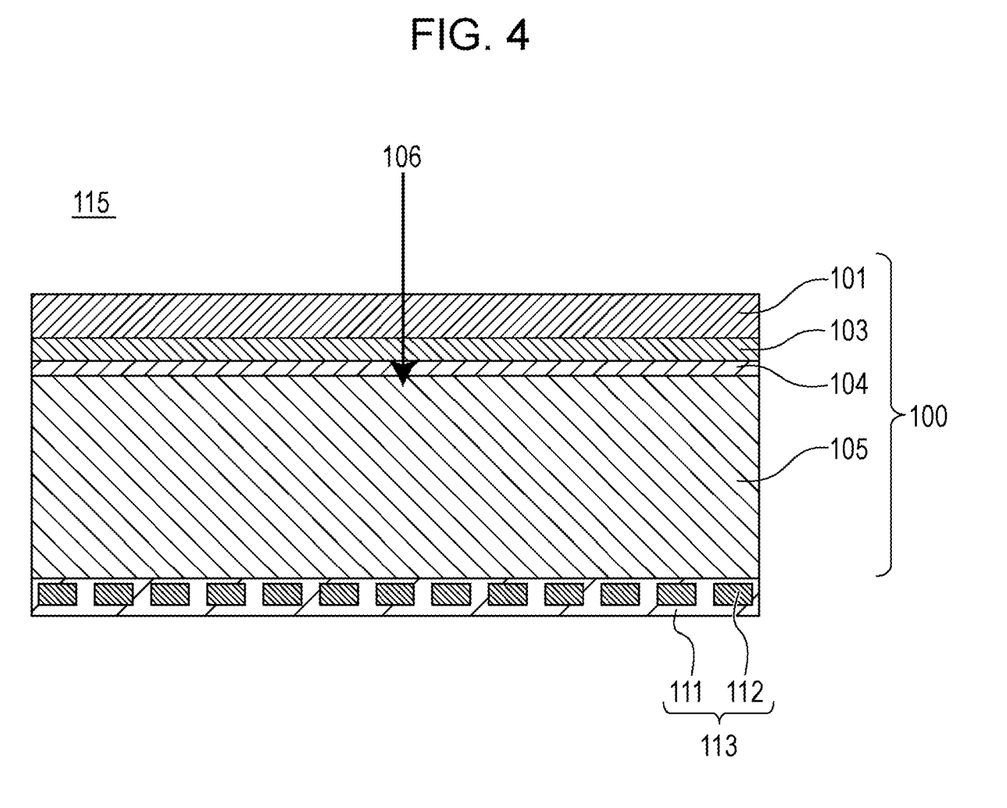
FIG. 4 is a schematic cross-sectional view of an embodiment of a radiation detector according to the present disclosure.

As illustrated in FIG. 4, the scintillator unit 100 and the detecting unit 113 for detecting light from the scintillator unit 100 can constitute a radiation detector 115. The detecting unit 113 includes a substrate 111 and light-receiving devices 112 arranged in two directions on the substrate 111. The detecting unit 113 is adjacent to the surface facing the low-refractive-index layer via the scintillator 105. A polymer protective layer can be located at the boundary between the detecting unit 113 and the scintillator 105 to protect the detecting unit 113. A fiber optic plate (FOP) or the like can also be used.

EXEMPLARY EMBODIMENTS

Although a scintillator unit according to the present disclosure is described in detail in the following exemplary embodiments, the present disclosure is not limited to these exemplary embodiments.

Exemplary Embodiment 1

<Preparation of Scintillator>

A scintillator was prepared on a base by a heating evaporation method, as described below. A heating boat in a vacuum chamber was filled with a CsI raw powder. A base placed opposite the boat was a glass substrate and was mounted on a rotary table. The vacuum chamber was once evacuated to a high vacuum of 1×10$^{-3}$ Pa or less with a vacuum pump, and the boat temperature was set at 670° C. Another boat was placed in the vacuum chamber, was filled with a thallium iodide (TlI) raw powder serving as a luminescent center, and was heated for simultaneous film formation. The raw materials were deposited on a 50-mm square glass substrate during rotation at 60 rpm.

Hollow silica particles with a silica outer shell were selected as particles for forming a low-refractive-index layer. A coating liquid for film formation was prepared using Thrulya 4110 (dispersion medium: IPA, silica solid content: 20.5% by mass, number-average particle size of one hollow particle: 60 nm, porosity of one hollow particle: 45%, refractive index of one hollow particle: 1.25) manufactured by JGC Catalysts and Chemicals Ltd. A dispersion liquid thus prepared may be referred to as a hollow silica particle dispersion liquid.

A film of the hollow silica particle dispersion liquid was formed on the prepared scintillator by a spin coating method to form a low-refractive-index layer. The film was formed at a substrate rotational speed of 1500 rpm for 15 seconds.

<Formation of Supporting Member (Reflective Layer)>

A supporting member was formed by covering the scintillator with aluminum (Al) held on a poly(ethylene terephthalate) (PET) film with a thickness of approximately 30 μm. The aluminum serves as a reflective layer. To improve adhesion to the scintillator on which the low-refractive-index layer was formed, a thermoplastic resin film with a thickness of approximately 30 μm was formed in advance before the formation of the supporting member. Adhesion between the scintillator, the reflective layer, and the supporting member was improved by heating with a vacuum laminator in the temperature range of 80° C. to 100° C.

<Structural Evaluation>

Figure 5A:
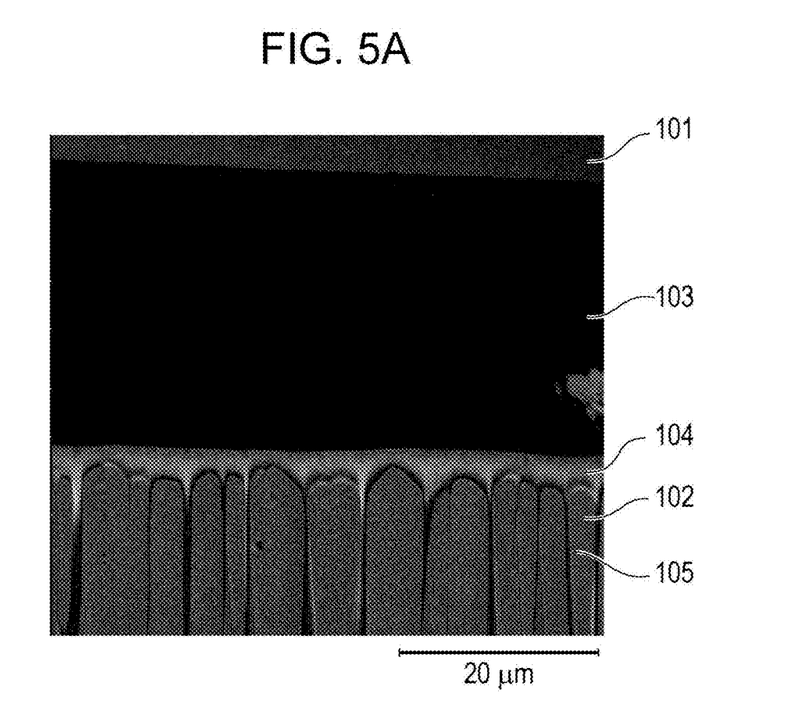
FIG. 5A is a scanning electron microscope (SEM) image of a scintillator unit according to the present disclosure.
Figure 5B:
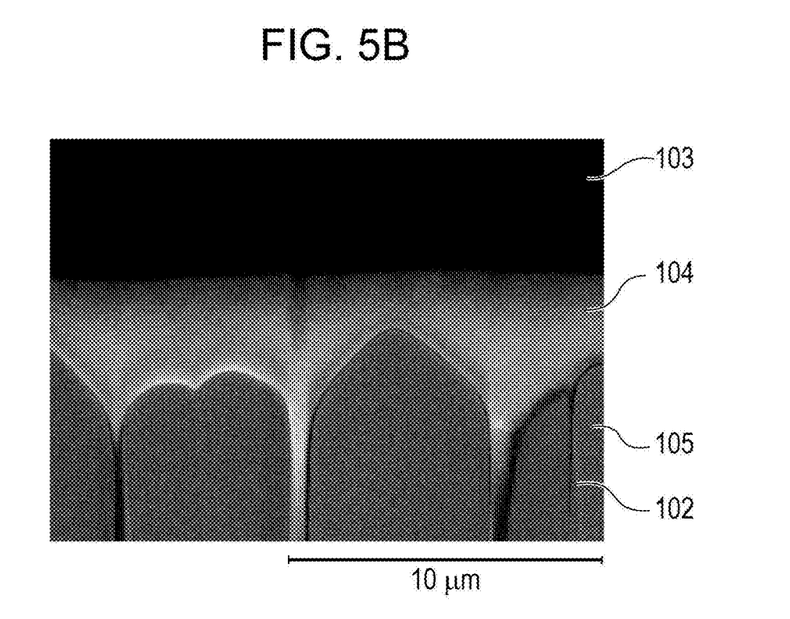
FIG. 5B is a magnified scanning electron microscope (SEM) image of a scintillator unit according to the present disclosure.

The prepared scintillator unit was subjected to slicing (8 kV-3 mA, 2 hours) with a triple ion milling apparatus (Leica EM-TIC-3X). Subsequently, to remove deposits, finishing ion beam slicing (30 kV-0.1 nA) was performed in the focused ion beam processing apparatus (FIB-SEM, manufactured by FEI Company, Nova 600). An SEM image was then acquired with a scanning electron microscope (hereinafter referred to as an SEM) at an accelerating voltage of 2 kV. FIG. 5A shows a low-magnification SEM image, and FIG. 5B shows a high-magnification SEM image near the interface of the low-refractive-index layer. The adhesive layer, the low-refractive-index layer, and CsI columnar crystals were closely bonded. The low-refractive-index layer was flat and filled the gap at end portions of the CsI columnar crystals. The average distance from the top of each columnar crystal to the interface between the low-refractive-index layer and the adhesive layer is defined as the thickness (T1) of the low-refractive-index layer. T1 calculated by measuring the distance for 30 CsI columnar crystals was 2.0 μm in Exemplary Embodiment 1. Furthermore, the average distance T3 was calculated to be 17 μm by measuring the distance from the interface between the low-refractive-index layer and a non-low-refractive-index layer portion located between the 30 CsI columnar crystals for which T1 was calculated to the interface between the low-refractive-index layer and the adhesive layer. The penetration depth T2 in the gap between the columnar crystals of the low-refractive-index layer was obtained by subtracting T1 from T3 and was 15 μm.

A cross-sectional SEM image was obtained under high magnification under which individual hollow particles could be observed. The hollow particles and the space between the hollow particles were distinguished by binarization of a gray scale image, and the area of each region was calculated. The porosity of the low-refractive-index layer was calculated to be 67% in consideration of the calculated area of the hollow particles and the volume fraction of the internal space relative to the total volume of the hollow particles. The refractive index of the low-refractive-index layer was calculated to be 1.15 using the formula (2) wherein ns was 1.46.

<MTF Evaluation and Sensitivity Evaluation>

The prepared scintillator unit was irradiated with X-rays to perform modulation transfer function (MTF) evaluation and sensitivity evaluation. A typical edge method was used for the MTF evaluation. The MTF was evaluated at 2 LP/mm by irradiating the scintillator with X-rays at a tube voltage of 80 kV and using an image formed on a light-receiving device with an optical system focused on the surface of the scintillator on the light extraction surface side.

<Preparation of Radiation Detector>

A polyimide layer was formed as a polymer protective layer by spin coating on a sensor panel including a detecting unit. A scintillator was formed on the polyimide layer. A low-refractive-index layer was then formed on the scintillator and was bonded with a vacuum laminator to an Al reflective layer via an adhesive layer (a layer containing a thermoplastic resin) to form a radiation detector.

Exemplary Embodiment 2

Exemplary Embodiment 2 was the same as Exemplary Embodiment 1 except that the substrate rotational speed of the spin coating was changed to 1000 rpm for 15 seconds to form the low-refractive-index layer.

Exemplary Embodiment 3

Exemplary Embodiment 3 was the same as Exemplary Embodiment 1 except that the film was formed by spraying five times by a spray method to form the low-refractive-index layer.

Exemplary Embodiment 4

Exemplary Embodiment 4 was the same as Exemplary Embodiment 1 except that a coating liquid prepared by diluting the hollow silica particle dispersion liquid with IPA to a silica solid content of 10.0% by mass was used and the film was formed by spraying 20 times by a spray method to form the low-refractive-index layer.

Exemplary Embodiment 5

Exemplary Embodiment 5 was the same as Exemplary Embodiment 1 except that the reflective layer was formed of an epoxy resin containing titanium oxide serving as an adhesive layer that also functions as the reflective layer. Exemplary Embodiment 5 corresponds to the structure according to the present disclosure illustrated in FIGS. 2A and 2B.

Exemplary Embodiment 6

AEROSIL R812 (manufactured by Nippon Aerosil Co., Ltd.), which are fumed silica particles with a methyl group on the surface thereof, was used for the hollow silica particle dispersion liquid to form the low-refractive-index layer. Fumed silica particles dispersed in propylene glycol monomethyl ether (PGME) at a solid content of 6.88% by mass and a solvent were enclosed in a glass vessel together with zirconia ($ZrO_2$) balls with a diameter of 0.5 mm. The glass vessel was rotated on a ball mill rotary table at a rotational speed of 30 rpm for 48 hours to disperse the fumed silica particles. A fumed silica particle dispersion liquid prepared by the dispersion treatment with the ball mill was used as a coating liquid. Exemplary Embodiment 6 was the same as Exemplary Embodiment 1 except that the film was formed by spraying the coating liquid five times by a spray method to form the low-refractive-index layer.

Figure 6:
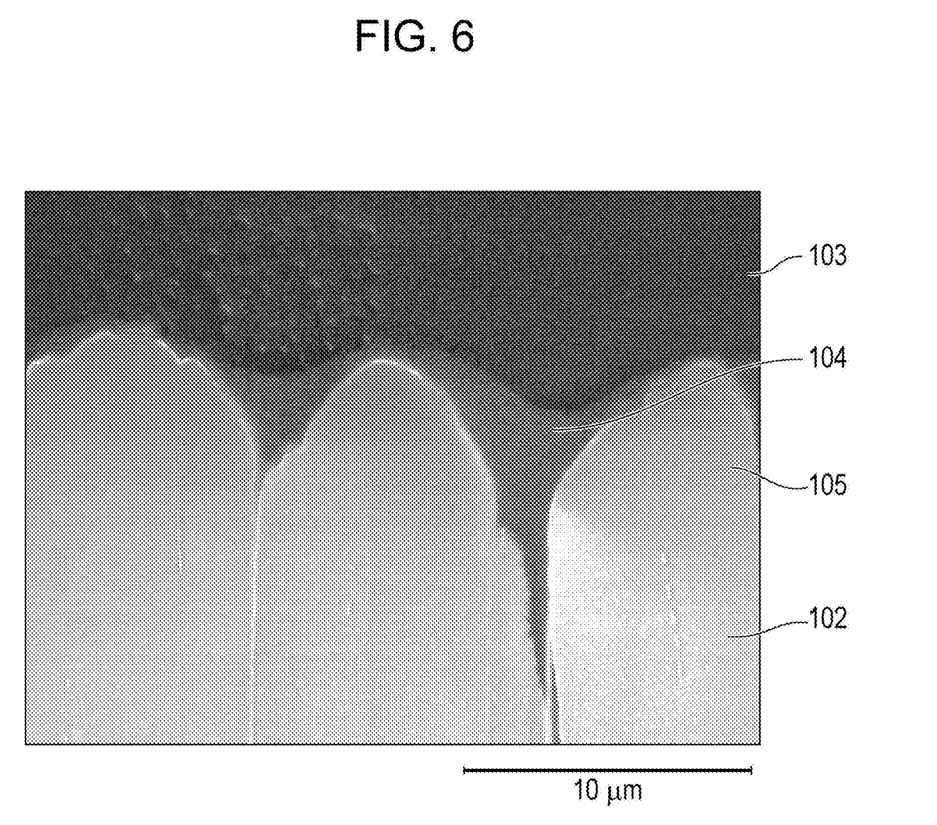
FIG. 6 is an SEM image of a scintillator unit according to the present disclosure.

FIG. 6 shows a cross-sectional SEM image acquired by the same method as in Exemplary Embodiment 1. The low-refractive-index layer is formed along the asperities at end portions of the CsI columnar crystals. The low-refractive-index layer in the spin coating method (FIGS. 5A and 5B) is formed to fill the gap between the columnar crystals and to have a flat surface, which becomes the interface with the adhesive layer in a later step, whereas the low-refractive-index layer in the spray method (FIG. 6) is formed along the asperities of the columnar crystals.

Comparative Example 1

Comparative Example 1 was the same as Exemplary Embodiment 1 except that the low-refractive-index layer was not formed.

Comparative Example 2

A thick low-refractive-index layer was formed. The fumed silica particle dispersion liquid in Exemplary Embodiment 6 was used as a coating liquid, and a film was formed by the spin coating method in the same manner as in Exemplary Embodiment 1.

Table 1 summarizes the MTF and sensitivity evaluation results of Exemplary Embodiments 1 to 6 and Comparative Examples 1 and 2. The film thickness is the average thickness (T1) from the top of each CsI columnar crystal. The MTF and sensitivity evaluation values are ratios to the known structure without the low-refractive-index layer according to Comparative Example 1.

(Discussions)

In Exemplary Embodiment 1, the low-refractive-index layer improved the MTF by 15% and the sensitivity by 10%. This is because the low-refractive-index layer on the CsI increases the total reflection efficiency at the interface between the CsI and the low-refractive-index layer and increases the amount of light remaining in the CsI. Light leaking into the adhesive layer propagates parallel to the surface of the light-receiving portion while repeatedly reflecting and attenuating in the adhesive layer, thus resulting in a decrease in sensitivity (=light attenuation) and a decrease in MTF. The low-refractive-index layer can decrease the amount of light leaking into the adhesive layer and improve the sensitivity and MTF.

[Film-Forming Method]

Exemplary Embodiments 1 to 4 are compared to show a difference due to the film-forming method. The spin coating method in Exemplary Embodiments 1 and 2 had higher sensitivity than the spray method in Exemplary Embodiments 3 and 4. In the spray method, droplets of the sprayed coating liquid are deposited on end portions of the columnar crystals, and regions without the low-refractive-index layer are scattered on the scintillator. In contrast, in the spin coating method, the low-refractive-index layer is formed over the entire surface of the scintillator. Thus, the scintillator unit formed by the spin coating method is less likely to leak light into the adhesive layer. Exemplary Embodiment 4, which had a higher frequency of spraying than Exemplary Embodiment 3, had larger regions with the low-refractive-index layer and had higher sensitivity.

[Type of Silica Particles]

Exemplary Embodiments 3, 4, and 6 are compared to show a difference due to the type of silica particles. When the film-forming method was the spray method, the fumed silica in Exemplary Embodiment 6 had a higher improvement rate of the MTF than the hollow silica in Exemplary Embodiments 3 and 4. This is probably because the low-refractive-index layer formed of the fumed silica had a lower refractive index than the low-refractive-index layer formed of the hollow silica and had a higher total reflection efficiency at the interface between the CsI scintillator and the low-refractive-index layer. However, the low-refractive-index layer formed of the hollow silica often has higher strength. This is because in a bound material of the hollow particles and the binder the binder located at the contact points between the hollow particles contributes strongly to the binding between the hollow particles and improves the strength of the film.

[Thickness of Low-Refractive-Index Layer]

Exemplary Embodiments 1 to 4 and 6 and Comparative Example 2 are compared to show a difference due to the MTF was improved by 22% in Exemplary Embodiment 6 with a film thickness of 0.5 µm but was decreased in Comparative Example 2 with a film thickness of 16 µm. Thus, the low-refractive-index layer with a thickness of at least 0.5 µm contributes sufficiently to the improvement of the MTF. On the other hand, Comparative Example 2 with an excessively large film thickness had a long optical path length of light reflected by the reflective layer, had light diffused in the transverse direction, and had a decrease in the MTF.

[Reflective Layer]

Exemplary Embodiments 1 and 5 are compared to show a difference due to the reflective layer. The adhesive layer with the reflection and adhesion functions in Exemplary Embodiment 5 also played the role of the reflective layer, caused no leakage light propagating through the adhesive layer, accordingly decreased light attenuation, consequently increased the amount of light reaching a light detecting unit, and greatly improved the sensitivity. Half of the light generated by the scintillator travels toward the light detecting unit, whereas the other half travels in the opposite direction. In contrast to the former, the latter had a long optical path to reach the light detecting unit and, when the adhesive layer also serving as the reflective layer was used, also had light scattering, and therefore had lower MTF than the other exemplary embodiments with the Al reflective layer.

TABLE 1

|  | Type of silica particles | Coating liquid concentration [wt %] | Film-forming conditions | Film thickness [µm] | Reflective layer | Sensitivity | MTF |
| --- | --- | --- | --- | --- | --- | --- | --- |
| Exemplary embodiment 1 | Hollow silica | 20.5 | Spin coating: 1500 rp-15 s | 2.0 | Al | 1.10 | 1.15 |
| Exemplary embodiment 2 | Hollow silica | 20.5 | Spin coating: 1000 rpm-15 s | 3.1 | Al | 1.07 | 1.15 |
| Exemplary embodiment 3 | Hollow silica | 20.5 | Spray: 5 times | 0.6 | Al | 0.96 | 1.11 |
| Exemplary embodiment 4 | Hollow silica | 10.0 | Spray: 20 times | 1.0 | Al | 1.04 | 1.15 |
| Exemplary embodiment 5 | Hollow silica | 20.5 | Spin coating: 1500 rpm-15 s | 2.0 | Adhesive layer containing TiO2 | 1.63 | 1.03 |
| Exemplary embodiment 6 | Fumed silica | 15.0 | Spray: 5 times | 0.5 | Al | 1.00 | 1.22 |
| Comparative example 1 | Without low-refractive-index layer | — | — | — | Al | 1.00 | 1.00 |
| Comparative example 2 | Fumed silica | 15.0 | Spin coating: 1500 rpm-15 s | 16.0 | Al | 0.99 | 0.88 | thickness of the low-refractive-index layer (film thickness). When the thickness of the low-refractive-index layer was changed using the hollow silica (Exemplary Embodiments 1 to 4), the MTF was improved by 11% in Exemplary Embodiment 3 with a film thickness of 0.6 µm and by 15% in Exemplary Embodiments 1, 2, and 4 with a thickness of 1.0 µm or more.

When the thickness of the low-refractive-index layer was changed using the fumed silica (Exemplary Embodiment 6 and Comparative Example 2), as compared with Comparative Example 1 without the low-refractive-index layer, the Thus, the present disclosure can provide a radiation detector with improved sensitivity and resolution.

The present disclosure can provide a scintillator unit with less light leakage from a scintillator into an adhesive layer and a radiation detector that can improve sensitivity to radiation and the resolution of an image to be formed.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

The invention claimed is:

1. A scintillator unit comprising:
   a supporting member, an adhesive layer, a low-refractive-index layer, and a scintillator in this order in an incident direction of radiation, wherein
   the low-refractive-index layer has a lower refractive index than a refractive index of the adhesive layer.

2. The scintillator unit according to claim 1, wherein
   the scintillator contains a plurality of columnar crystals, and
   the low-refractive-index layer is located between an end portion of each columnar crystal in an extending direction and the adhesive layer.

3. The scintillator unit according to claim 1, wherein at least part of the supporting member includes a reflective layer or a light-absorbing layer.

4. The scintillator unit according to claim 1, wherein the adhesive layer includes a scattering layer containing light-scattering particles and a binder resin.

5. The scintillator unit according to claim 1, wherein the adhesive layer contains a thermoplastic resin.

6. The scintillator unit according to claim 1, wherein the adhesive layer contains an acrylic resin.

7. The scintillator unit according to claim 1, wherein the low-refractive-index layer contains silicon dioxide.

8. The scintillator unit according to claim 1, wherein the low-refractive-index layer contains hollow particles.

9. The scintillator unit according to claim 8, wherein the hollow particles have an outer shell with a refractive index of 1.60 or less.

10. The scintillator unit according to claim 8, wherein the hollow particles have an outer shell with a refractive index of 1.35 or more.

11. The scintillator unit according to claim 1, wherein the low-refractive-index layer has a porosity in the range of 60.0% to 95.0%.

12. The scintillator unit according to claim 1, wherein the low-refractive-index layer has a thickness in the range of 300 nm to 5 μm.

13. The scintillator unit according to claim 1, wherein the low-refractive-index layer contains fumed silica particles.

14. A radiation detector comprising:
    a supporting member, an adhesive layer, a low-refractive-index layer, a scintillator, and a detecting unit for detecting light generated from the scintillator in this order, wherein
    the low-refractive-index layer has a lower refractive index than a refractive index of the adhesive layer, and
    the detecting unit faces the low-refractive-index layer via the scintillator.

15. A scintillator unit comprising:
    an adhesive layer between a scintillator and a supporting member, wherein
    a low-refractive-index layer containing silicon dioxide with a lower refractive index than the adhesive layer is located between the scintillator and the adhesive layer.

16. A radiation detector comprising:
    a scintillator unit including an adhesive layer between a scintillator and a supporting member; and
    a detecting unit for detecting light generated from the scintillator,
    wherein the scintillator unit includes a low-refractive-index layer containing silicon dioxide with a lower refractive index than the adhesive layer between the scintillator and the adhesive layer, and
    the detecting unit faces the low-refractive-index layer via the scintillator.

* * * * *